US 10,925,575 B2

(12) United States Patent
Pandey et al.

(10) Patent No.: US 10,925,575 B2
(45) Date of Patent: Feb. 23, 2021

(54) CONNECTORS ALLOWING ACOUSTIC OR DIGITAL TRANSMISSION FOR A STETHOSCOPE

(71) Applicant: Indian Institute of Technology Bombay, Mumbai (IN)

(72) Inventors: Tapas Pandey, Dehradun (IN); Adarsha Kachappily, Chikmagalur (IN); Rupesh Ghyar, Nashik (IN); Bhallamudi Ravi, Mumbai (IN); Nambiraj Konar, Mumbai (IN); Lancelot Pinto, Mumbai (IN)

(73) Assignee: Indian Institute of Technology Bombay, Mumbai (IN)

( * ) Notice: Subject to any disclaimer, the term of this patent is extended or adjusted under 35 U.S.C. 154(b) by 0 days.

(21) Appl. No.: 16/424,476

(22) Filed: May 28, 2019

(65) Prior Publication Data

US 2019/0274656 A1 Sep. 12, 2019

Related U.S. Application Data

(63) Continuation of application No. PCT/IN2017/050558, filed on Nov. 27, 2017.

(30) Foreign Application Priority Data

Nov. 27, 2016 (IN) .............................. 201621029618

(51) Int. Cl.
| A61B 7/04 | (2006.01) |
| A61B 5/00 | (2006.01) |
| A61B 7/00 | (2006.01) |
| A61B 7/02 | (2006.01) |
| A61B 5/08 | (2006.01) |

(52) U.S. Cl.
CPC .............. *A61B 7/04* (2013.01); *A61B 5/7225* (2013.01); *A61B 7/003* (2013.01); *A61B 7/02* (2013.01); *A61B 5/08* (2013.01); *A61B 5/7203* (2013.01)

(58) Field of Classification Search
CPC .. A61B 7/02; A61B 7/026; A61B 7/04; A61B 7/003; A61B 5/7225; A61B 5/08; A61B 5/0803; A61B 5/7203; H04R 1/46
(Continued)

(56) References Cited

U.S. PATENT DOCUMENTS 3,247,324 A * 4/1966 Cefaly ..................... A61B 7/02
  381/67
3,539,724 A * 11/1970 Keesee .................... A61B 7/02
  381/67

(Continued)

FOREIGN PATENT DOCUMENTS

WO  2015065988  5/2015

OTHER PUBLICATIONS

WIPO, International Search Report in corresponding PCT application PCT/IN2017/050558, dated Jan. 29, 2018.
(Continued)

*Primary Examiner* — Jason R Kurr
(74) *Attorney, Agent, or Firm* — Ryan Alley IP

(57) ABSTRACT

Connectors permits acoustic and digital stethoscope transmissions. Connectors include first and second pieces for the stethoscope chest piece and earpiece channels. The first piece has a moveable inner element with openings and includes a channel in line with the chest piece channel to provide an acoustic mode of functioning. The openings are collinear with the inner element channel and the extruded channels. The extruded channels and inner element channel may be arrayed in a line and have diameters that successively decrease. A transducer inside the inner element blocks sound from the first extruded channel, and a second transducer is inside the inner element on the other side of one of the openings. For an electronic mode of functioning, the first transducer is in line with the chest piece extruded channel (Continued)

and the second transducer is in line with the earpiece extruded channel. A switch may switch between the modes.

36 Claims, 13 Drawing Sheets

(58) Field of Classification Search
USPC .............................................. 381/67; 181/131
See application file for complete search history.

(56) References Cited

U.S. PATENT DOCUMENTS

| | | | | |
|---|---|---|---|---|
| 4,071,694 | A | * | 1/1978 | Pfeiffer .................... A61B 7/02 381/67 |
| 5,774,563 | A | * | 6/1998 | DesLauriers .......... A61B 7/026 381/67 |
| 5,910,992 | A | * | 6/1999 | Ho ........................ A61B 7/026 181/131 |
| 9,486,180 | B2 | * | 11/2016 | Ting ........................ A61B 7/02 |
| 9,973,847 | B2 | * | 5/2018 | Wong ....................... A61B 7/04 |
| 2015/0297171 | A1 | | 10/2015 | Thiagarajan |
| 2016/0078779 | A1 | | 3/2016 | Sahai et al. |

OTHER PUBLICATIONS

WIPO, Written Opinion of the ISA in corresponding PCT application PCT/IN2017/050558, dated Jan. 29, 2018.

* cited by examiner

CONNECTORS ALLOWING ACOUSTIC OR DIGITAL TRANSMISSION FOR A STETHOSCOPE

RELATED APPLICATIONS

This application claims priority under 35 U.S.C. § 120 to, and is a continuation of, co-pending International Application PCT/IN2017/050558, filed Nov. 27, 2017 and designating the US, which claims priority to Indian Application 201621029618, filed Nov. 27, 2016, such IN Application also being claimed priority to under 35 U.S.C. § 119. These IN and International applications are incorporated by reference herein in their entireties.

BACKGROUND

Auscultation is the technique to hear internal body sounds of body. Using auscultation, a physician can tell about an abnormality in a body. Auscultation is performed for the purposes of examining the circulatory and respiratory systems, such as via heart and breath sounds, as well as the gastrointestinal system, such as via bowel sounds.

Auscultation is a skill that requires substantial clinical experience, a fine stethoscope, and good listening skills. Health professionals like doctors, nurses, etc., listen to three main organs and organ systems during auscultation: the heart; the lungs; and the gastrointestinal system.

A stethoscope is an acoustic medical device for auscultation—listening to the internal sounds of an animal or human body. It typically has a small disc-shaped resonator that is placed against the chest, and two tubes connected to earpieces. It is often used to listen to lung and heart sounds. It is also used to listen to intestines and blood flow in arteries and veins. In combination with a sphygmomanometer, it is commonly used for measurements of blood pressure.

An electronic stethoscope (or stethophone) overcomes the low sound levels by electronically amplifying body sounds. Electronic stethoscopes require conversion of acoustic sound waves to electrical signals which can then be amplified and processed for optimal listening.

SUMMARY

Example embodiments include connectors for acoustic and digital stethoscope transmissions. Connectors may include first and second pieces coupled to the chest piece and earpiece of the stethoscope through extruded channels. The first piece may include a moveable inner element with openings on the first and second pieces. The inner element may include a channel in line with the extruded channel of the chest piece to provide an acoustic mode of functioning. The openings may be collinear with the inner element channel and the extruded channels. The extruded channels and inner element channel may be arrayed in a line and have diameters that successively decrease, such as in a direction of sound. A transducer inside the inner element may substantially block acoustic transmission from the first extruded channel, while a second transducer is inside the inner element on the other side of one of the openings. In another position for an electronic mode of functioning, the first transducer may be in line with the chest piece extruded channel and the second transducer is in line with the earpiece extruded channel. A switch may move the inner element between the modes.

BRIEF DESCRIPTION OF THE DRAWINGS

Example embodiments will become more apparent by describing, in detail, the attached drawings, wherein like elements are represented by like reference numerals, which are given by way of illustration only and thus do not limit the terms which they depict.

DETAILED DESCRIPTION

Figure 1:
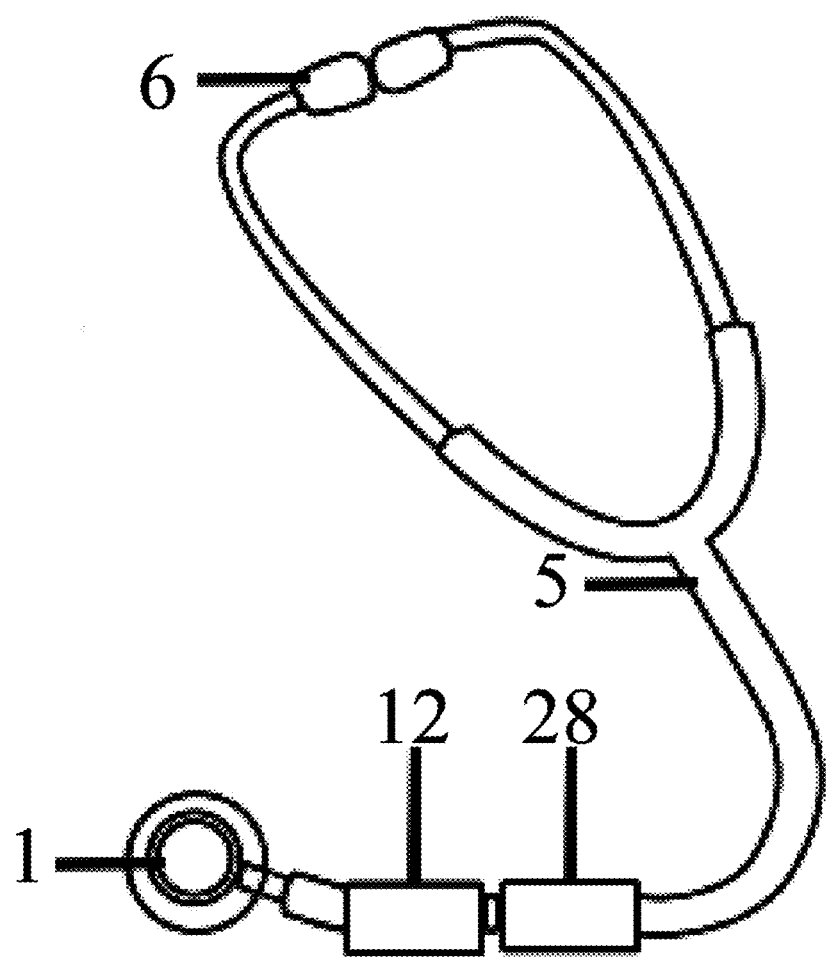
FIG. 1 illustrates a perspective view of an example embodiment stethoscope along with connector.
Figure 2:
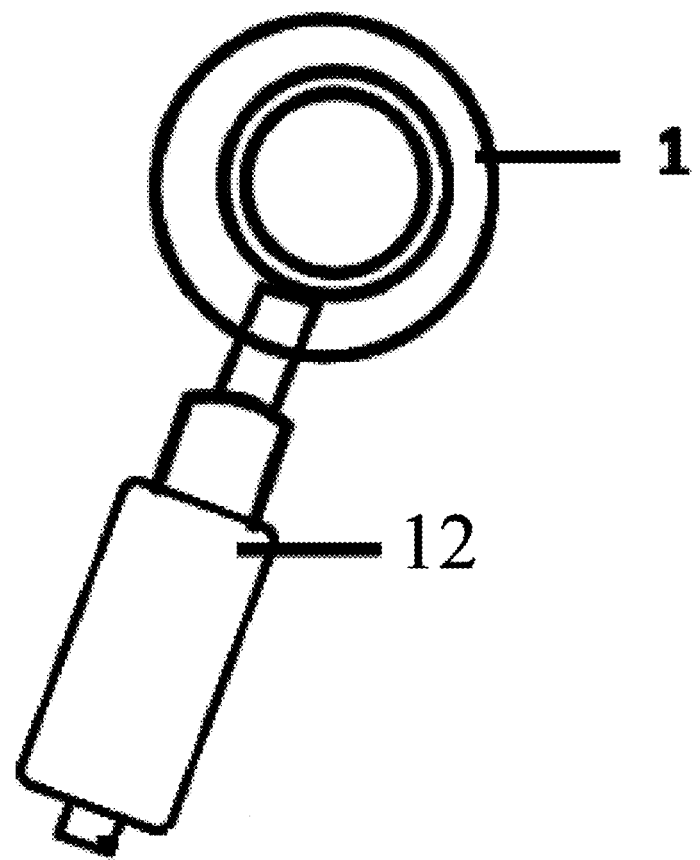
FIG. 2 illustrates a view showing a first part connected to the stem of the stethoscope chest piece.
Figure 3:
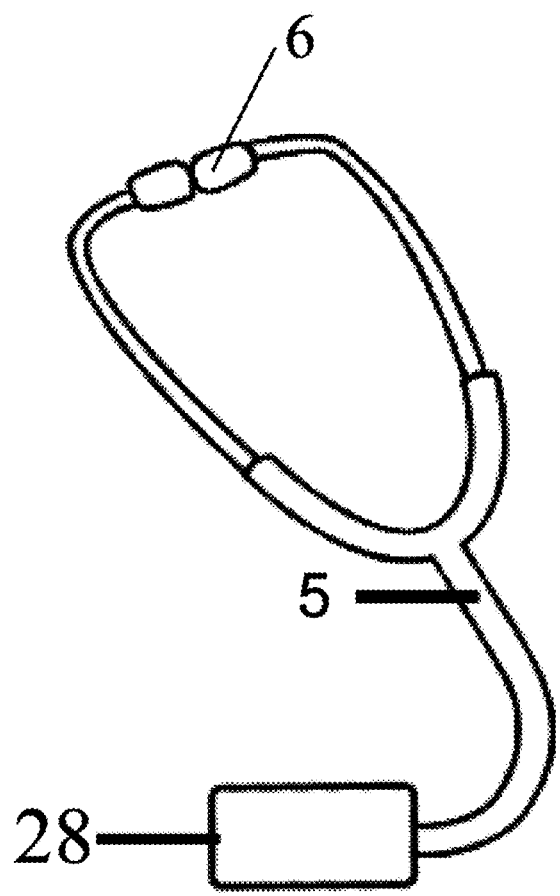
FIG. 3 illustrates a view showing a second part connected to the stethoscope tubing which connects to an earpiece.
Figure 4:
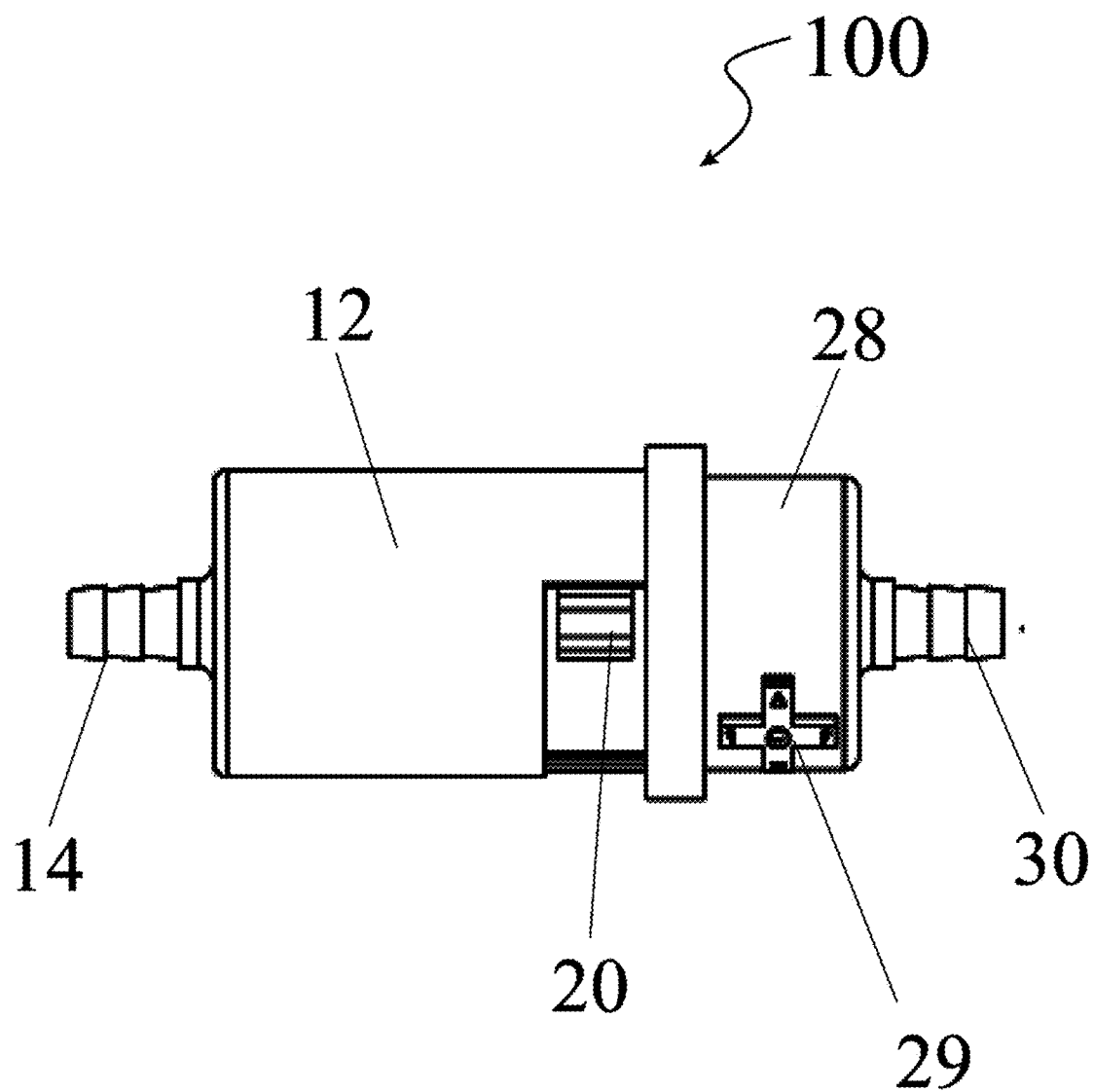
FIG. 4 illustrates a schematic view of the connector.
Figure 5A:
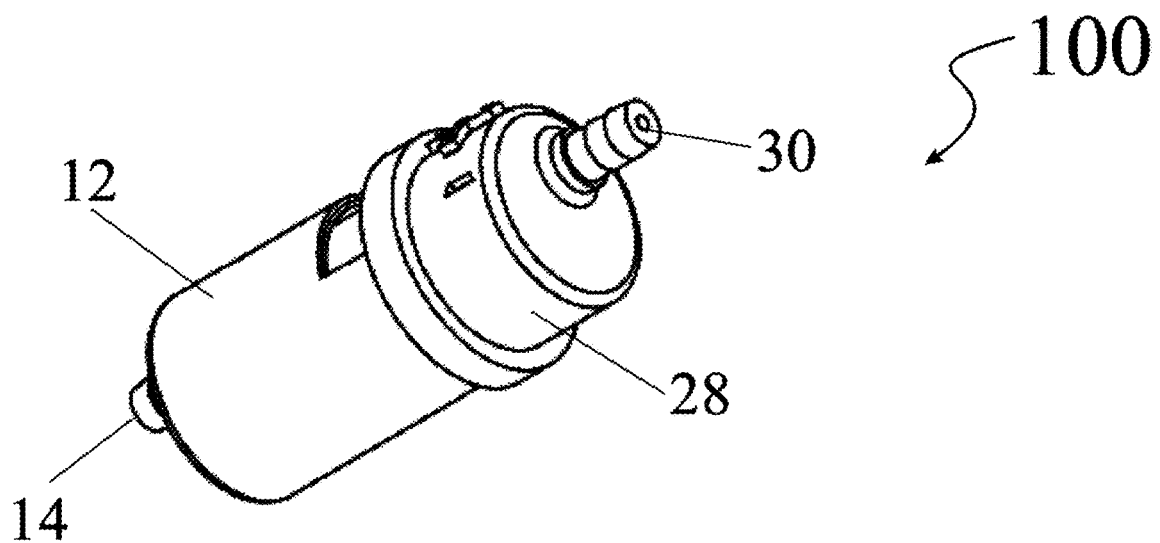
FIG. 5A illustrates another schematic view, from the earpiece side, of the connector.
Figure 5B:
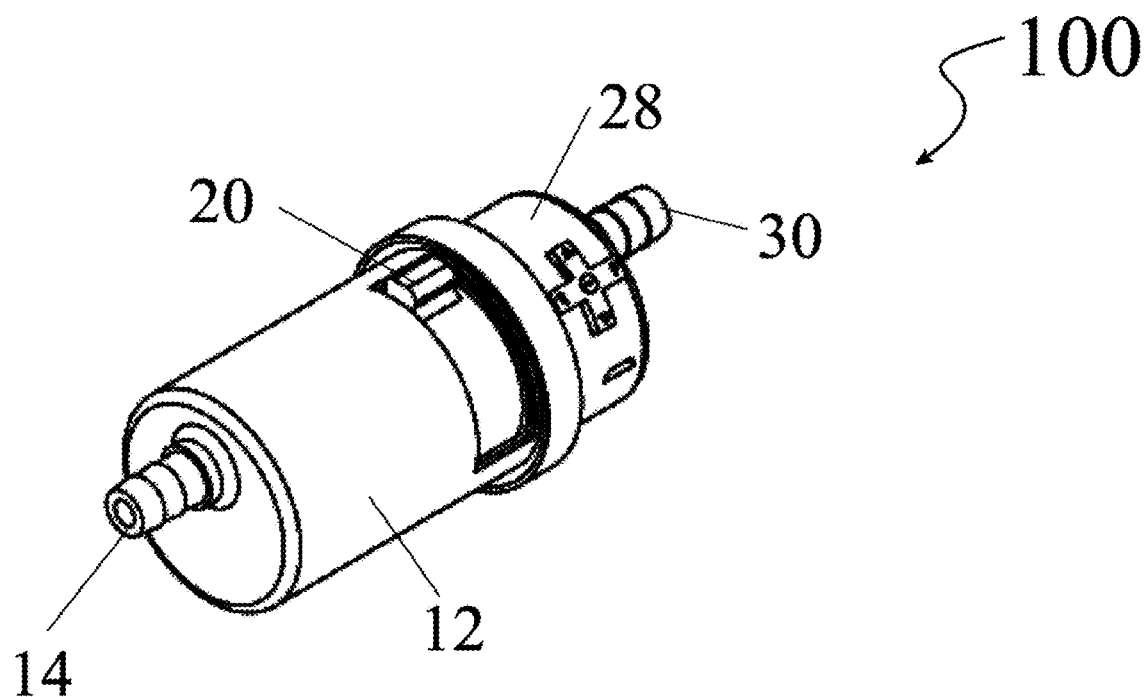
FIG. 5B illustrates another schematic view, from a chest piece side, of the connector.
Figure 6:
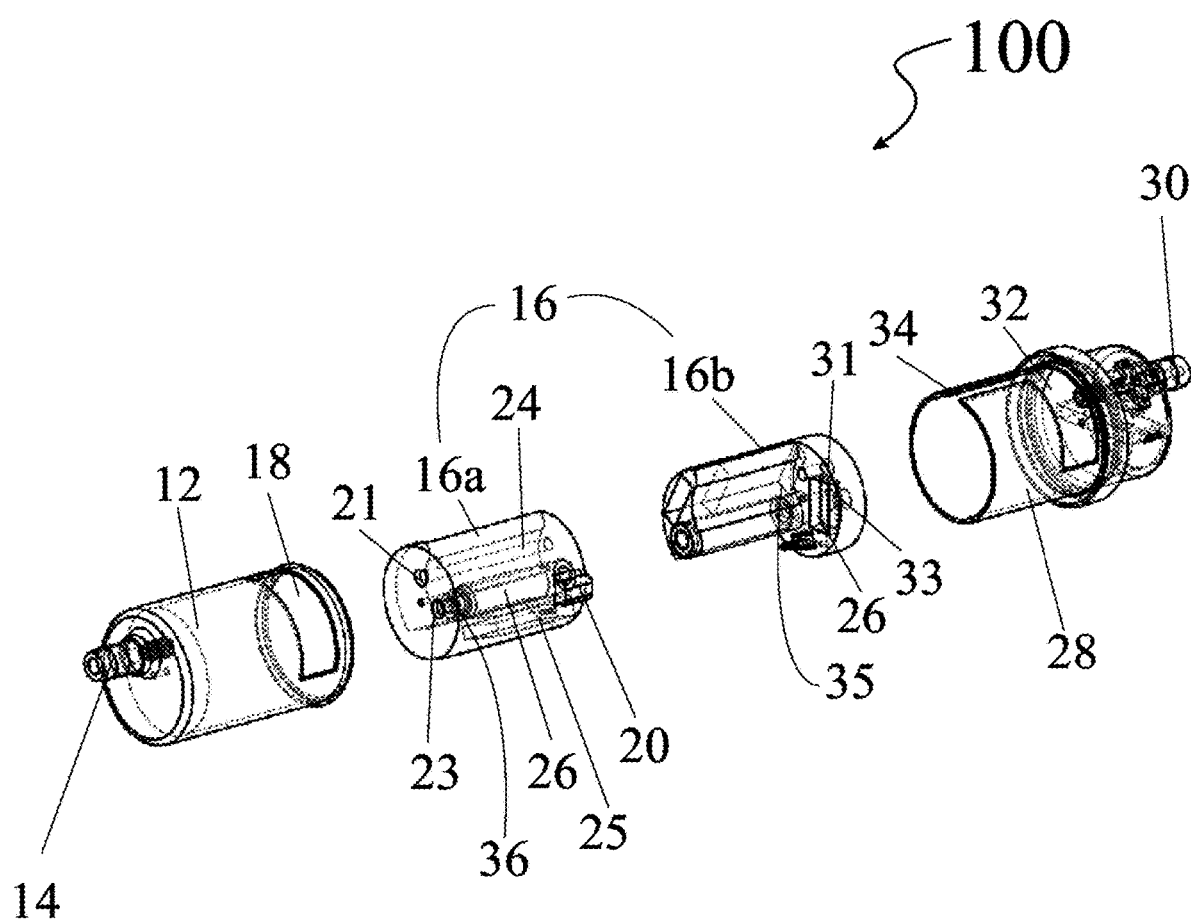
FIG. 6 illustrates a schematic exploded view of the connector depicting the first part and the second part.
Figure 7:
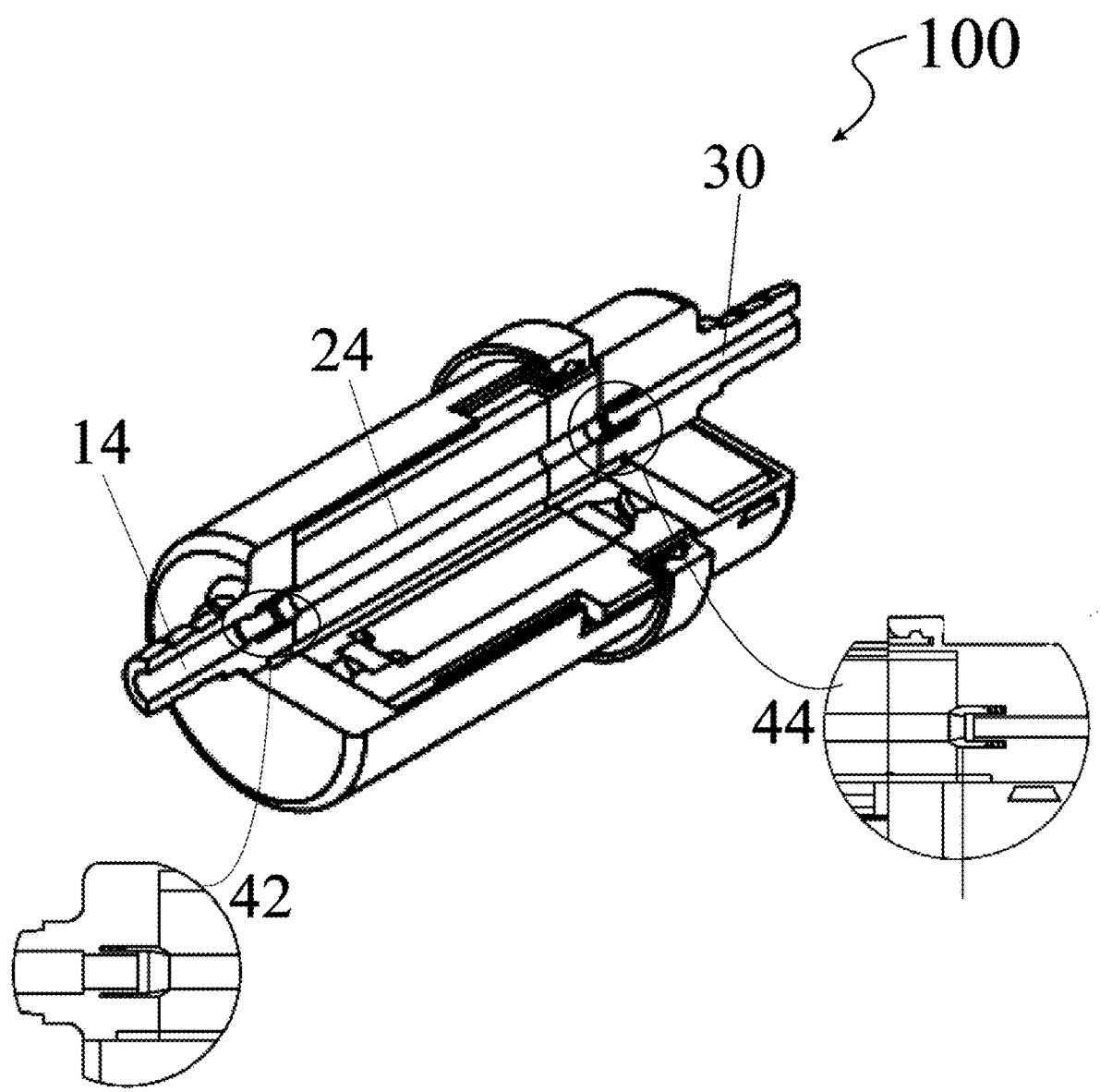
FIG. 7 illustrates a schematic cut-section view of the connector when it is used in an acoustic/mechanical mode.
Figure 8:
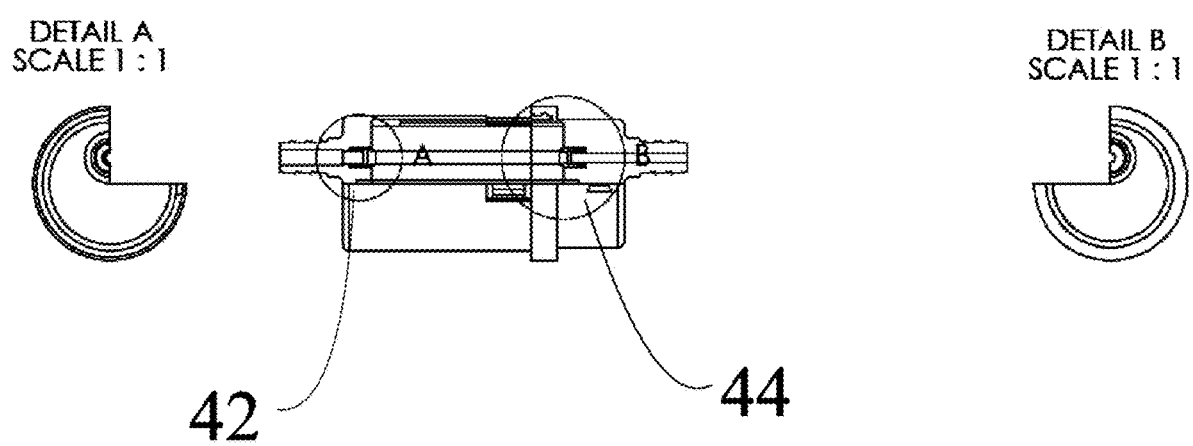
FIG. 8 illustrates a schematic cut-section view of the connector when it is used in an acoustic/mechanical mode, wherein the changes in transmission channel profile can be seen.
Figure 9:
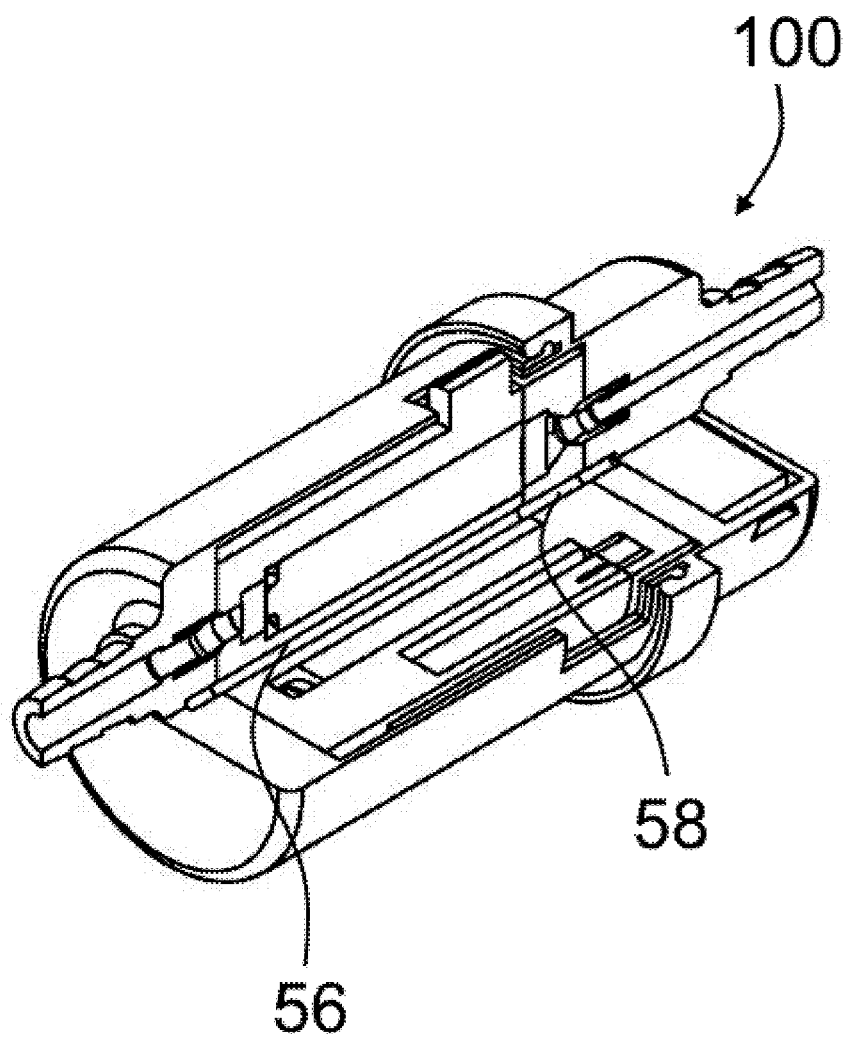
FIG. 9 illustrates a schematic cut-section view of the connector when it is used in an electronic wired mode.
Figure 10:
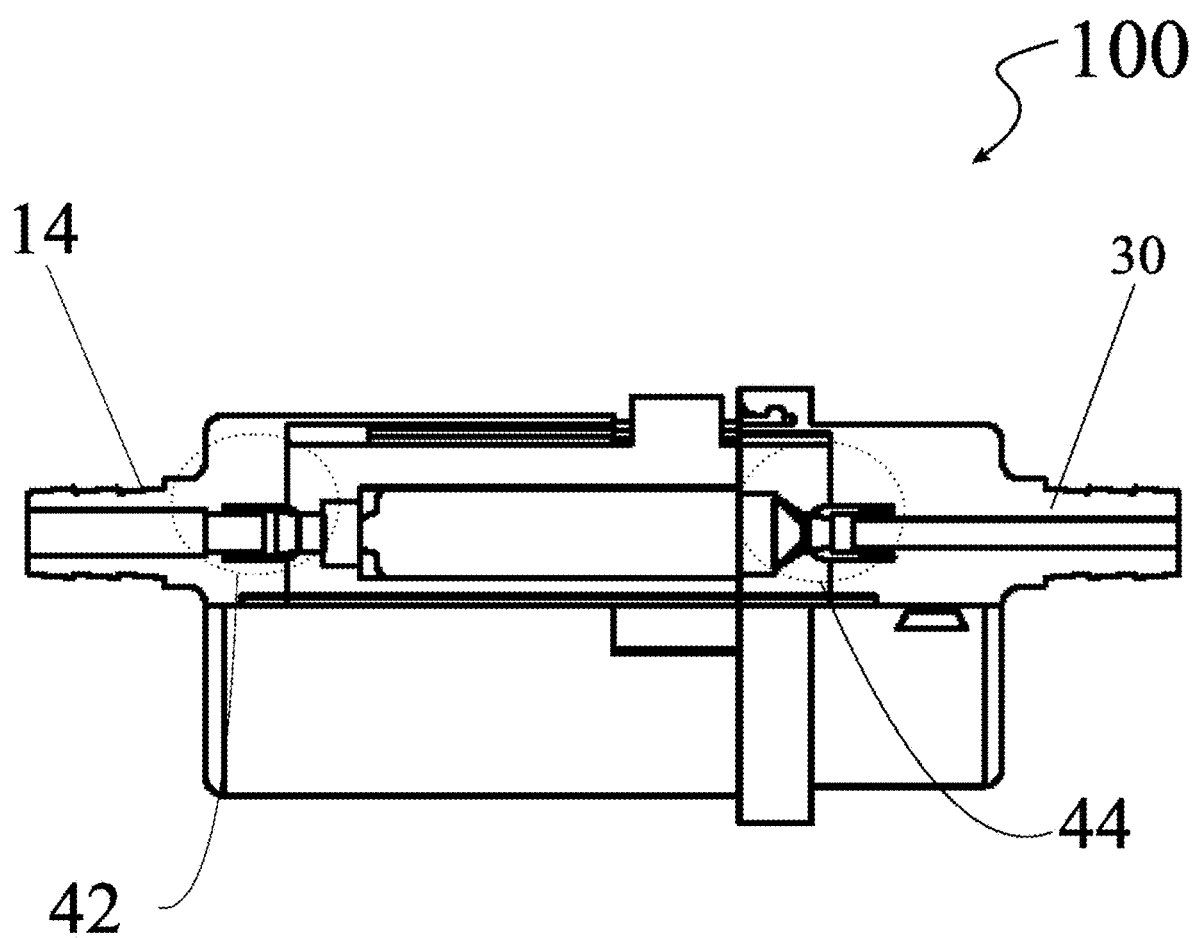
FIG. 10 illustrates another schematic cut-section view of the connector when it is used in the electronic wired mode.
Figure 11A:
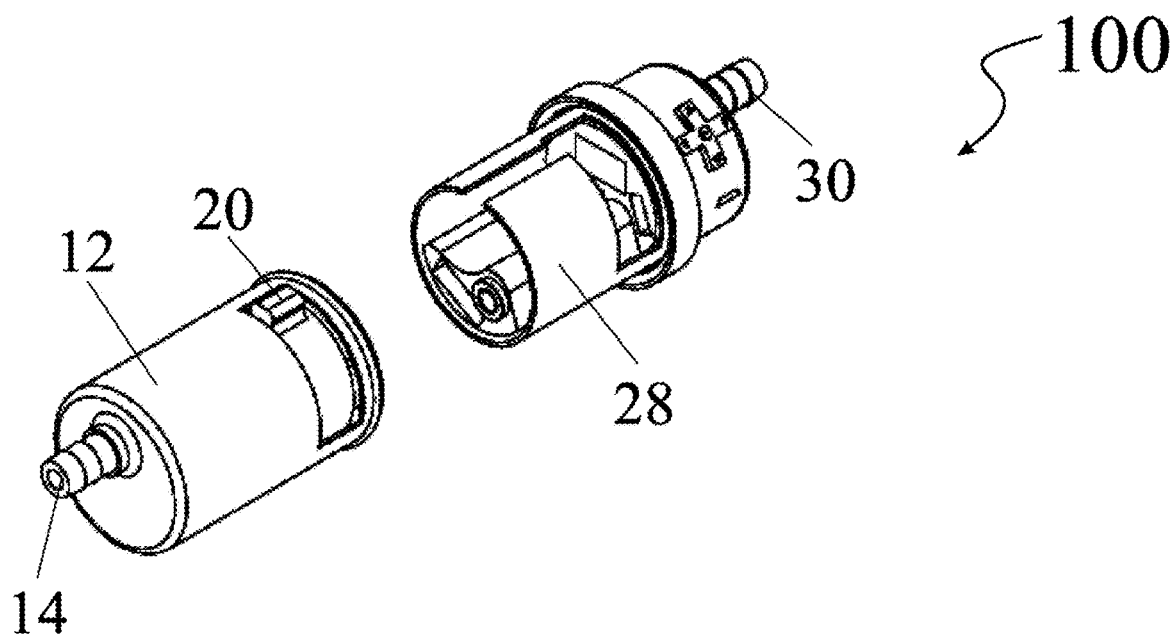
FIGS. 11A and 11B illustrate schematic views of the connector when it is used in a split electronic wireless mode.
Figure 11B:
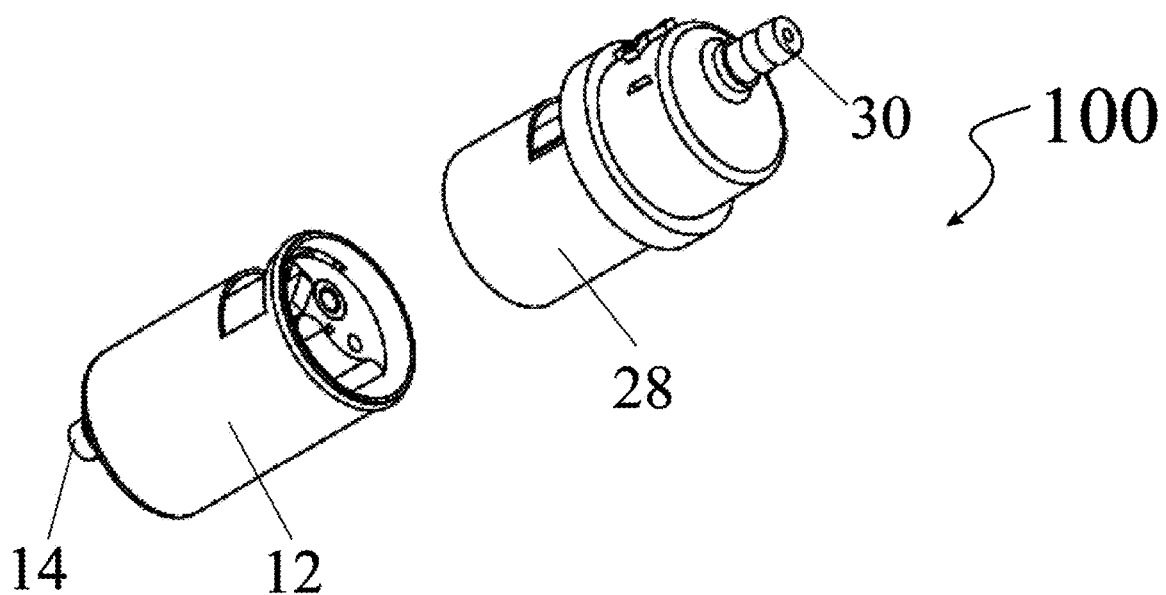

Because this is a patent document, general, broad rules of construction should be applied when reading it. Everything described and shown in this document is an example of subject matter falling within the scope of the claims, appended below. Any specific structural and functional details disclosed herein are merely for purposes of describing how to make and use examples. Several different embodiments and methods not specifically disclosed herein may fall within the claim scope; as such, the claims may be embodied in many alternate forms and should not be construed as limited to only examples set forth herein.

It will be understood that, although the ordinal terms "first," "second," etc. may be used herein to describe various elements, these elements should not be limited to any order by these terms. These terms are used only to distinguish one element from another; where there are "second" or higher ordinals, there merely must be that many number of elements, without necessarily any difference or other relationship. For example, a first element could be termed a second element, and, similarly, a second element could be termed a first element, without departing from the scope of example embodiments or methods. As used herein, the term "and/or" includes all combinations of one or more of the associated listed items. The use of "etc." is defined as "et cetera" and indicates the inclusion of all other elements belonging to the same group of the preceding items, in any "and/or" combination(s).

It will be understood that when an element is referred to as being "connected," "coupled," "mated," "attached," "fixed," etc. to another element, it can be directly connected to the other element, or intervening elements may be present. In contrast, when an element is referred to as being "directly connected," "directly coupled," etc. to another element, there are no intervening elements present. Other words used to describe the relationship between elements should be interpreted in a like fashion (e.g., "between" versus "directly between," "adjacent" versus "directly adjacent," etc.). Similarly, a term such as "communicatively connected" includes all variations of information exchange and routing between two elements, including intermediary devices, networks, etc., connected wirelessly or not. The term "digital" includes electronics or powered hardware having an electronic function with a wired or wireless configuration, whereas "mechanical" or "acoustic" includes no electronics.

As used herein, the singular forms "a," "an," and the are intended to include both the singular and plural forms, unless the language explicitly indicates otherwise. Indefinite articles like "a" and "an" introduce or refer to any modified term, both previously-introduced and not, while definite articles like "the" refer to the same previously-introduced term. It will be further understood that the terms "comprises," "comprising," "includes," and/or "including," when used herein, specify the presence of stated features, characteristics, steps, operations, elements, and/or components, but do not themselves preclude the presence or addition of one or more other features, characteristics, steps, operations, elements, components, and/or groups thereof.

The structures and operations discussed below may occur out of the order described and/or noted in the figures. For example, two operations and/or figures shown in succession may in fact be executed concurrently or may sometimes be executed in the reverse order, depending upon the functionality/acts involved. Similarly, individual operations within example methods described below may be executed repetitively, individually or sequentially, to provide looping or other series of operations aside from single operations described below. It should be presumed that any embodiment or method having features and functionality described below, in any workable combination, falls within the scope of example embodiments.

The Inventor has newly recognized that digital stethoscopes are mobile-dependant for simultaneous auscultation, which requires a specific design. For auscultation, the medical practitioner has to be within a certain distance because of the stethoscope tubing. During epidemics this becomes a problem for the medical due to communicable diseases. So there is a need for a connector which can convert an acoustic stethoscope into a wireless stethoscope with its chest piece side spaced apart from the earpiece side.

Separately, amplification of stethoscope contact artifacts and component cutoffs, such as frequency response thresholds of electronic stethoscope microphones, pre-amps, amps, and speakers, limits the overall utility of electronically-amplified stethoscopes by amplifying mid-range sounds, while simultaneously attenuating high- and low-frequency range sounds. To increase the amplitude and to record and analyse body sounds, a digital stethoscope is required which has gain which is very large than a conventional acoustic stethoscope. So there is a need for a connector which can convert any acoustic stethoscope into an electronic stethoscope. Example embodiments described below address these and other problems recognized by Inventors with unique solutions enabled by example embodiments.

The present invention is connectors that allow both acoustic and digital transmissions and methods of operating the same. In contrast to the present invention, the few examples discussed below illustrate just a subset of the variety of different configurations that can be used as and/or in connection with the present invention.

FIG. 1 illustrates a perspective view of an example embodiment stethoscope and connector. As shown in FIG. 1, connector 100 is configured to be communicatively coupled to chest piece 1, and the connector 100 further is configured to be connected to earpiece 6. Connector 100 may include first part 12 and second part 28. First part 12 may be communicatively coupled to chest piece 1, and second part 28 may be communicatively coupled to earpiece 6.

Connector 100 may be operated in the following three modes: Acoustic mechanical mode; Electronic wired mode; and Split Electronic wireless mode. In split electronic wireless mode, the connector may work in the following modes: one-to-one electronic wireless mode: communication between one chest piece and one earpiece; and one-to-many electronic wireless mode: communication between one chest piece and a plurality of earpieces or a plurality of remotely-located computational devices 91 or a plurality of remotely-located mobile devices 93.

First piece 12 may have an open-ended casing. For example, this may be a cylindrical casing. It may also be referred to as a chest-side casing or a chest-side piece. One end of this casing may be open-ended, which allows it to receive additional parts or components in a manner such that the first piece is a partial outer cover of connector 100. The other end of this casing may include first extruded channel 14, which may be coupled to a stethoscope tube extending from the chest piece of the stethoscope tube.

First piece 12 may include inner element 16 configured to be ensconced, at least partially, within first piece 12. So positioned, inner element 16 may be angularly displaceable within first piece 12. The angular displacement may be restricted by first slit 18 provided in first piece 12 and knob 20 that extends from inner element 16 through first slit 18. For example, first slit 18 may be a partial-circumferential slit, and inner element 16 may be a cylinder with a first end and a second end. The first end may include at least two openings 21 and 23, and the second end may include at least two openings 31 and 33.

Knob 20 may be a switching mechanism that switches connector 100, and hence the stethoscope, from an acoustic version to an electronic version. When knob 20 is in a first position, the connector works in an acoustic manner because first opening 21 is in line with extruded channel 14. First opening 21 may extend into inner element channel 24 that traverses the length of inner element 16. When the knob 20 is angularly displaced from the first position to a second position, inner element 16 also may correspondingly angularly displace, such that second opening 23 is in line with first extruded channel 14, thereby making the connector work in an electronic manner. In the electronic version, second opening 23 may be in line with first transducer 36 located in-line and just behind second opening 23.

Inner element 16 may include two parts 16a and 16b such that first inner element part 16a includes knob 20, inner element channel 24, and first transducer 36, while second inner element part 16b includes second transducer 26 along with receiver 35. For example, first inner element part 16a and second inner element part 16b may be complementary, in that second inner element part 16b slides into first inner element part 16a to be ensconced by first inner element part 16a, and the two parts may fit into each other. First inner element part 16a may include at least two openings 21 and 23. Second inner element part 16b may include at least two openings 31 and 33. As knob 20 moves from the first position to the second position, either inner element channel 24 is in line with first extruded channel 14 or first transducer 36 is in line with first extruded channel 14, thereby determining if the connector is to work in an acoustic manner or in an electronic manner.

The first inner element may be substantially a cylinder with one first-piece side disc end with two openings and a hollow second-piece side to receive the second inner element. The second inner element may be substantially a partial cylinder with a second-piece side disc end with two openings.

Alternatively, second piece 28 may be an open-ended casing, such as a cylindrical casing. It may also be referred to as an ear-side casing or an ear-side piece. One end of this casing may be an open-ended which allows it to receive additional parts or components in a manner such that the first piece is a partial outer cover of the connector and the second piece receives the inner element and also slides into the first piece as a middle layer. The other end of this casing includes second extruded channel 30 that may be coupled to a stethoscope tube extending from the earpiece of the stethoscope tube. Second slit 32 at one end of second piece 28 may correspond to first slit 18 of first piece 12, in that when second piece 28 is completely ensconced within first piece 12, first slit 18 and second slit 32 may overlap seamlessly, so as to define one single slit. This second slit may also be a partial-circumferential slit and extend in an orthogonal fashion, from one end parallel to the axis of the connector to form axis-wise channeled notch 34 that opens at the open-end of second piece 28. This may allow for the knob to securely slide out when first piece 12 is spaced apart from second piece 28, in the wireless configuration.

First inner element 16a may include first transducer along 36 and transmitter 25 at a chest-side end, for example, the end with first inner element 12. For example, first transducer 36 may be just behind second opening 23 such that first transducer 36 substantially or completely blocks any acoustic transmission from first extruded channel 14. In the electronic mode of operation, first extruded channel 14 and transducer 36 are collinear and co-axial and also abutting each other such that there is no acoustic loss outside the channel or from its transmission from one channel to the other.

Second inner element channel 26 may include second transducer 26 and receiver 35. In the acoustic mode of functioning, first extruded channel 14, inner element channel 24, and second extruded channel 30 may be collinear and co-axial. A diameter of first extruded channel 14 may be greater than a diameter of inner element channel 24. A diameter of inner element channel 24 may be greater than a diameter of second extruded channel 30. This narrowing in diameter across the channels and across the direction of traverse of sound/acoustic waves from the chest piece to the earpiece of the stethoscope may ensure that there is quasi-amplification of sound, because concentration of energy increases as sound/acoustic waves traverse from a larger area to a narrower area, thereby increasing concentration in energy of the sound/acoustic wave per unit volume.

First locking coupler 42 may provide locking and/or coupling between first extruded channel 14 and inner element channel 24. First coupler 42 may be in first piece 12, which can seal openings 21 and 23 when brought near the opening, due to spring action. The shape of the coupler may taper along the direction of sound, thereby increasing concentration in energy of the sound/acoustic wave per unit volume, when the sound is transmitted from first extruded channel 14 to second extruded channel 30. First locking coupler 42 may be a spring-loaded coupler and taper in its dimension along its longitudinal axis from first extruded channel 14 to inner element channel 24. Opening 21 may be the acoustic opening on the chest-piece side of inner element 16 and include a cam profile, such as a hemispherical cam profile that receives first locking coupler 41, which acts as a cam follower, to enable locking and coupling.

Second locking coupler 44 may provide locking and/or coupling between second extruded channel 30 and inner element channel 24. Second coupler 44 may be in second piece 28, which can seal openings 31 and 33 when brought near the opening, due to spring action. The shape of the coupler may taper along the direction of sound, thereby increasing concentration in energy of the sound/acoustic wave per unit volume when the sound is coming from first extruded channel 14 to second extruded channel 30. Second locking coupler 44 may be a spring-loaded coupler that tapers in its dimension along its longitudinal axis from inner element channel 24 to second extruded channel 30. Another opening 31 may be the acoustic opening on the ear-piece side of inner element 16 and may include a cam profile, such as a hemispherical cam profile to receive second locking coupler 44, which acts as a cam follower, to enable locking and coupling.

In the electronic mode of functioning, first transducer 36 may be in-line with the direction of sound, for example, in-line with first extruded channel 14. Also, in the electronic mode of functioning, second transducer 26 may be in-line with the direction of sound, for example, in line with second extruded channel 30.

An interlock may be provided to lock first piece 12 to second piece 28 to convert from an engaged acoustic mode to a split electronic wireless mode.

First centre rod 56 and second centre rod 58 may provide the support and the longitudinal axis along which the inner element angularly displaces itself. For example, first centre rod 56 may have its first end support at first piece 12 and its second end support at inner element 16. Second centre rod 58 may have its first end support at second piece 28 and its second end support at inner element 16 where first end rod 56 ends. First end rod 56 and second end rod 58 may be collinear and co-axial.

Figure 12:
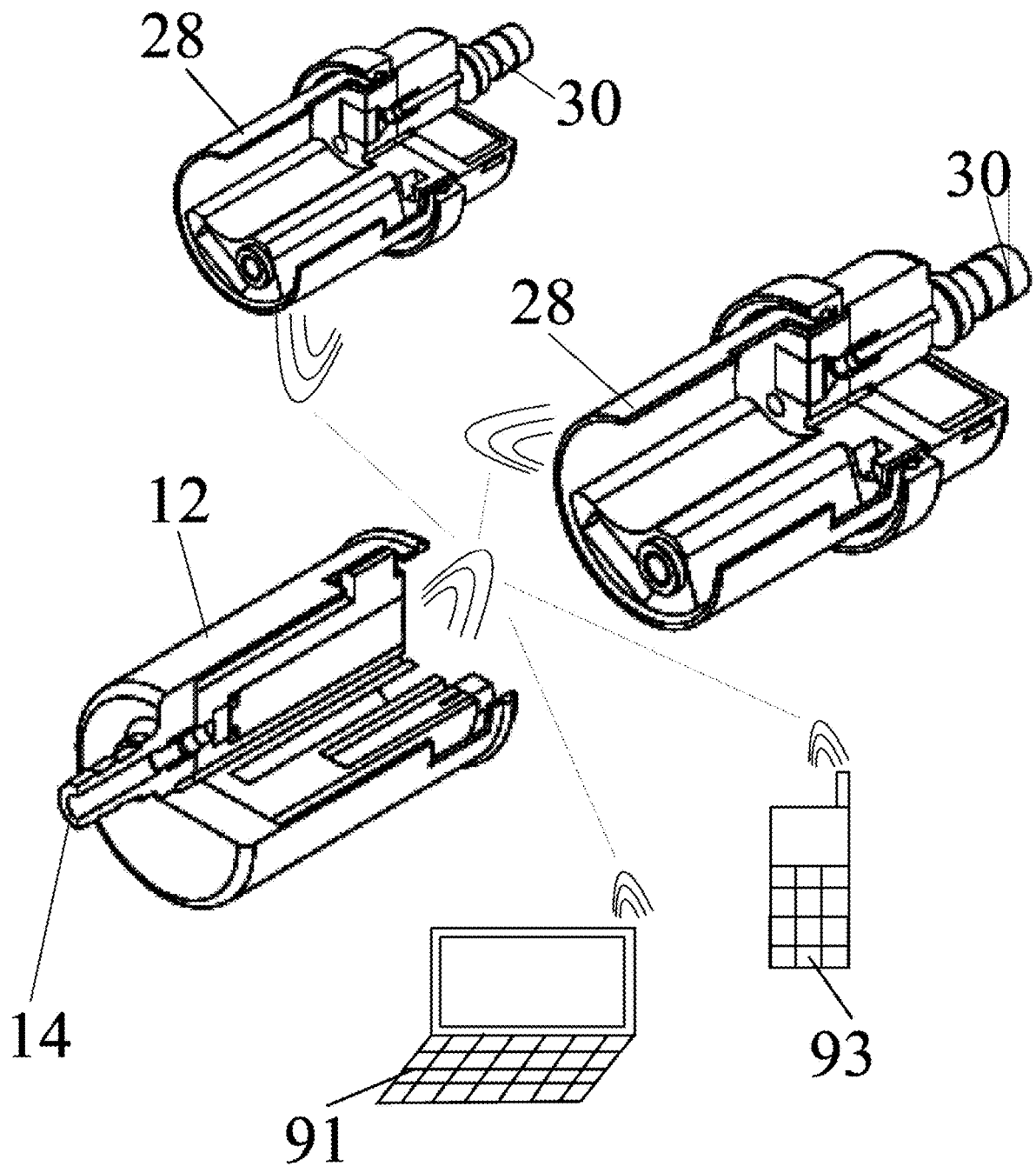
FIG. 12 illustrates a schematic cut-section view of the connector when it is used in the split electronic wireless mode.

FIG. 12 illustrates a schematic cut-section view of example embodiment connector 100 when used in a split electronic wireless mode. It shows a split view of the connector so that the chest piece is spaced apart from the earpiece. Multiple such earpieces can be used to sync with the chest piece since the connector can be split in a wireless fashion.

Figure 13:
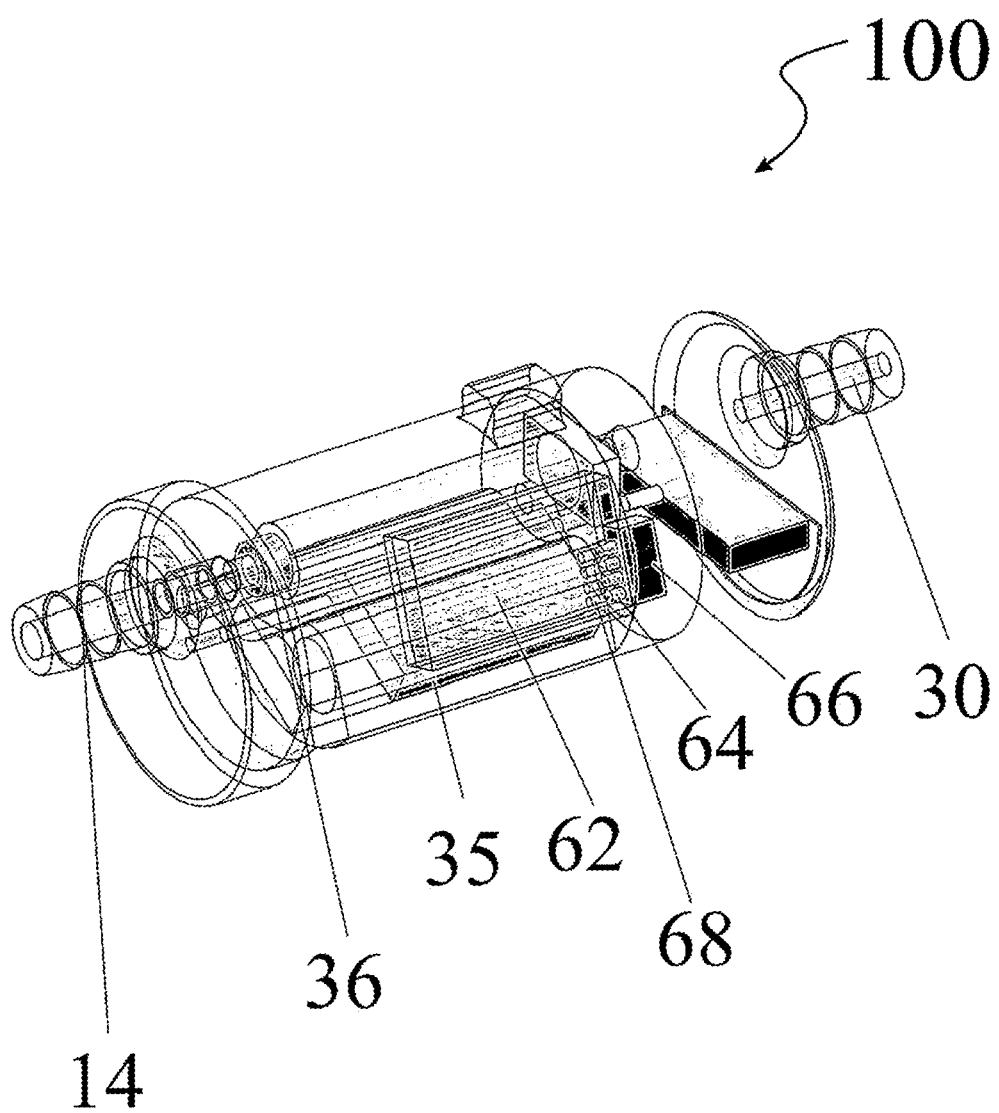
FIG. 13 illustrates a schematic view of the connector when it is used in the electronic wired mode.

FIG. 13 illustrates a schematic view of example embodiment connector 100 when in an electronic wired mode. In this mode, first extruded channel 14 and first transducer 36 may be in line. Second transducer 26 may be in line with second extruded channel 30. First electronic board 62 in first inner element 16a may receive connector pins 64 from second electronic board 66 in second inner element 16b. The speaker may be located in second inner element 16b. Slots 68 of first electronic board 62 may receive connector pins 64. Connector pins 64 may charge a battery which is used during the split electronic wireless mode of the connector, and the transmitter and receiver may not be activated, thereby saving battery.

Button 29 may include the functions of record, playback, etc. in its electronic mode of functioning. Noise cancellation may be provided via a third transducer or a second microphone which picks up surrounding noise and then uses active noise cancellation to reduce ambient noise. For example, this transducer may receive external noise.

As seen in FIGS. 1-13, when chest piece 1 is placed against a patient for sensing body sounds, it vibrates according to the patient's diaphragm, creating acoustic pressure waves which travel up to first part 12. In the acoustic mode of functioning, the waves may be transmitted through the channels to second part 28. The nature of the channels is such that amplification occurs at earpiece 6. In the electronic wired mode of functioning, the waves may be converted to an electrical signal by first transducer 36, processed, and transmitted to second transducer 26 where the electrical signal is converted to an acoustic signal for hearing at earpiece 6. In this mode, transmitter 25 and receiver 35 are not required. In the electronic wireless mode of functioning, the waves may be captured by first transducer 36, sent to transmitter 25 and wirelessly transmitted to second transducer 26 along with a receiver 35 or multiple such receivers 35.

Example embodiment connector 100 assists in transmission of body sound through conventional stethoscope, wirelessly. It allows switching between an acoustic mode and a digital mode by a switching mechanism. Additionally, it allows a wired digital mode as well as wireless digital mode. Example embodiment connector 100 also allows a one-to-many wireless digital mode wherein a single chest piece can transmit its readings to a plurality of remotely-located earpieces and/or remotely located computational or mobile devices.

Example embodiment connector 100 thus does not require a mobile device or an earphone for simultaneous auscultation. That is, example embodiments may be mobile-independent. A stethoscope earpiece with attachment can be used for simultaneous auscultation of body sounds, and the modular attachment design gives the flexibility of using the stethoscope in acoustic or electronic modes as well as wireless mode. Any stethoscope can be made as digital stethoscope through example embodiments in an acoustic mode, electronic wired mode, or electronic wireless mode. Example embodiment connectors cause the stethoscope to work in one-to-one electronic wireless modes with communication between one chest piece and one earpiece or one-to-many electronic wireless modes with communication between one chest piece and a plurality of earpieces, remotely-located computational devices, and/or remotely-located mobile devices.

In this way example embodiments can provide an auscultation device with a connector that converts any acoustic stethoscope into an electronic or a digital stethoscope. Example embodiment connectors may thus permit conventional auscultation as well as electronic recording, transmitting wireless information, and/or simultaneous hearing by multiple users. This may provide additional flexibility and improved auscultation through a modular attachment for any stethoscope that can be modified or switched to be used in analog or digital modes, regardless of distance from a patient. Example embodiment connectors may allow any acoustic stethoscope to function in split-mode by splitting a chest-piece side apart from an ear-piece side.

Example embodiments and methods thus being described, it will be appreciated by one skilled in the art that example embodiments may be varied and substituted through routine experimentation while still falling within the scope of the following claims. For example, although a typical stethoscope is used throughout the figures, it is understood that different acoustical pickups and membrane shapes are useable in example embodiments—and fall within the scope of the claims. Such variations are not to be regarded as departure from the scope of these claims.

The invention claimed is:

1. A connector permitting acoustic and digital transmission from a stethoscope, the connector comprising:
   a first piece communicatively coupled to a chest piece of the stethoscope through a first extruded channel;
   a second piece communicatively coupled to an earpiece of the stethoscope through a second extruded channel;
   an inner element at least partially within the first piece and displaceable within the first piece, wherein the inner element includes at least two first-piece end openings on an end of the first piece and at least two second-piece end openings on an end of the second piece;
   an inner element channel within the inner element in line with the first extruded channel and the second extruded channel, in a first position to provide an acoustic mode of functioning, wherein one of the first-piece end openings and second-piece end openings are collinear with the inner element channel, the first extruded channel, and the second extruded channel, and wherein the first extruded channel, the inner element channel, and the second extruded channel have diameters that decrease in a direction of sound;
   a first transducer inside the inner element past one of the first-piece end openings to substantially block acoustic transmission from the first extruded channel;
   a second transducer inside the inner element before one of the second-piece end openings, wherein, in a second position, the first transducer is in line with the first extruded channel and the second transducer is configured to be in line with the second extruded channel to provide an electronic mode of functioning; and
   a switch configured to displace the inner element between the first position and the second position so as to switch the connector between the acoustic mode and the electronic mode, wherein the inner element includes at least a first inner element and a second inner element, wherein the first inner element includes the first transducer and a transmitter at a chest-side end behind the second opening so that in the electronic mode of operation, the first extruded channel and the transducer are collinear, co-axial, and abutting each to prevent acoustic loss outside the channel.

2. The connector of claim 1, wherein the switch is configured to displace the inner element in one of angular displacement and linear displacement.

3. The connector of claim 2, wherein the first piece includes a first partial-circumferential slit to provide the angular displacement.

4. The connector of claim 1, wherein the switch is a knob extending from the inner element, wherein the knob is configured to displace the inner element by angularly displacing the inner element between the first position and the second position, and wherein the knob extends from the inner element through a first partial-circumferential slit.

5. The connector of claim 1, wherein the inner element includes at least one of, a first transducer and a transmitter, and a second transducer and a receiver.

6. The connector of claim 1, wherein the inner element is a cylinder with a first end and a second end, wherein the first end includes at least two openings, and wherein the second end includes at least two openings.

7. The connector of claim 1, wherein, in the first position, a first opening is in line with the first extruded channel and extends into the inner element channel that traverses a length of the inner element, and wherein, in the second position, a second opening is in line with the first extruded channel and in line with the first transducer in-line and behind the second opening.

8. The connector of claim 1, wherein, the inner element includes a first inner element part and a second inner element part that are complementary such that the second inner element part slides into the first inner element part, and wherein the first inner element part includes at least two openings and the second inner element part includes at least two openings.

9. The connector of claim 1, wherein when the switch moves from the first position to the second position, the inner element channel is in line with the first extruded channel, and wherein when the switch moves from the second position to the first position, the first transducer is in line with the first extruded channel.

10. The connector of claim 1, wherein the second piece includes a second slit and the first piece includes a first slit corresponding to the second slit such that when the second piece is completely within the first piece, the first slit and the second slit overlap seamlessly, and wherein the second slit is a partial-circumferential slit and extending orthogonally from its one end, parallel to the axis of the connector to form an axis-wise channelled notch that opens at the open-end of the second piece.

11. The connector of claim 1, wherein the first inner element is spaced apart from the second inner element so as to achieve a split electronic wireless mode of functioning.

12. The connector of claim 1, wherein, in the acoustic mode of functioning, the first extruded channel, the inner element channel, and the second extruded channel are collinear and co-axial.

13. The connector of claim 1, further comprising:
a first locking coupler, wherein the inner element includes a first end and a second end, wherein the first end includes at least two openings and wherein the second end includes at least a first acoustic opening on the first piece side of the inner element that includes a hemispherical cam profile to receive a first locking coupler.

14. The connector of claim 1, wherein in the electronic mode of functioning, the first extruded channel and the first transducer are in line and the second transducer is in line with the second extruded channel.

15. The connector of claim 1, wherein in the electronic mode of functioning, the first transducer is in line with direction of sound and the first extruded channel, and wherein the second transducer is in-line with the direction of sound and, in line with the second extruded channel.

16. A connector permitting acoustic and digital transmission from a stethoscope, the connector comprising:
a first piece communicatively coupled to a chest piece of the stethoscope through a first extruded channel;
a second piece communicatively coupled to an earpiece of the stethoscope through a second extruded channel;
an inner element at least partially within the first piece and displaceable within the first piece, wherein the inner element includes at least two first-piece end openings on an end of the first piece and at least two second-piece end openings on an end of the second piece;
an inner element channel within the inner element in line with the first extruded channel and the second extruded channel, in a first position to provide an acoustic mode of functioning, wherein one of the first-piece end openings and second-piece end openings are collinear with the inner element channel, the first extruded channel, and the second extruded channel, and wherein the first extruded channel, the inner element channel, and the second extruded channel have diameters that decrease in a direction of sound;
a first transducer inside the inner element past one of the first-piece end openings to substantially block acoustic transmission from the first extruded channel;
a second transducer inside the inner element before one of the second-piece end openings, wherein, in a second position, the first transducer is in line with the first extruded channel and the second transducer is configured to be in line with the second extruded channel to provide an electronic mode of functioning;
a switch configured to displace the inner element between the first position and the second position so as to switch the connector between the acoustic mode and the electronic mode; and
a first locking coupler locking and coupling between the first extruded channel and the inner element channel, wherein the first locking coupler is in the first piece in communication with an opening of the inner element that is in communication with the first extruded channel, and wherein the first locking coupler is a spring-loaded coupler and tapering in its dimension along its longitudinal axis from the first extruded channel to an inner element channel.

17. The connector of claim 16, wherein the inner element includes a first end and a second end, wherein the first end includes at least two openings, and wherein the second end includes at least a first acoustic opening on the first piece side of the inner element that includes a hemispherical cam profile to receive a first locking coupler.

18. The connector of claim 16, wherein, in the first position, a first opening is in line with the first extruded channel and extends into the inner element channel that traverses a length of the inner element, and wherein, in the second position, a second opening is in line with the first extruded channel and in line with the first transducer in-line and behind the second opening.

19. The connector of claim 16, wherein, when the switch moves from the first position to the second position, the inner element channel is in line with the first extruded channel, and wherein when the switch moves from the second position to the first position, the first transducer is in line with the first extruded channel.

20. The connector of claim 16, wherein, in the acoustic mode of functioning, the first extruded channel, the inner element channel, and the second extruded channel are collinear and co-axial, and wherein, in the electronic mode of functioning, the first transducer is in line with direction of sound and the first extruded channel, and wherein the second transducer is in-line with the direction of sound and, in line with the second extruded channel.

21. A connector permitting acoustic and digital transmission from a stethoscope, the connector comprising:
a first piece communicatively coupled to a chest piece of the stethoscope through a first extruded channel;
a second piece communicatively coupled to an earpiece of the stethoscope through a second extruded channel;
an inner element at least partially within the first piece and displaceable within the first piece, wherein the inner element includes at least two first-piece end openings on an end of the first piece and at least two second-piece end openings on an end of the second piece;
an inner element channel within the inner element in line with the first extruded channel and the second extruded channel, in a first position to provide an acoustic mode of functioning, wherein one of the first-piece end openings and second-piece end openings are collinear with the inner element channel, the first extruded channel, and the second extruded channel, and wherein the first extruded channel, the inner element channel, and the second extruded channel have diameters that decrease in a direction of sound;
a first transducer inside the inner element past one of the first-piece end openings to substantially block acoustic transmission from the first extruded channel;
a second transducer inside the inner element before one of the second-piece end openings, wherein, in a second position, the first transducer is in line with the first extruded channel and the second transducer is configured to be in line with the second extruded channel to provide an electronic mode of functioning;
a switch configured to displace the inner element between the first position and the second position so as to switch the connector between the acoustic mode and the electronic mode; and
a first locking coupler locking and coupling between the second extruded channel and the inner element channel, wherein the first locking coupler is a spring-loaded coupler and tapering in its dimension along its longitudinal axis from an inner element channel to the second extruded channel.

22. The connector of claim 21, wherein the inner element includes a first end and a second end, wherein the first end includes at least two openings, and wherein the second end includes at least a first acoustic opening on the first piece side of the inner element that includes a hemispherical cam profile to receive a first locking coupler.

23. The connector of claim 21, wherein, in the first position, a first opening is in line with the first extruded channel and extends into the inner element channel that traverses a length of the inner element, and wherein, in the second position, a second opening is in line with the first extruded channel and in line with the first transducer in-line and behind the second opening.

24. The connector of claim 21, wherein, when the switch moves from the first position to the second position, the inner element channel is in line with the first extruded channel, and wherein when the switch moves from the second position to the first position, the first transducer is in line with the first extruded channel.

25. The connector of claim 21, wherein, in the acoustic mode of functioning, the first extruded channel, the inner element channel, and the second extruded channel are collinear and co-axial, and wherein, in the electronic mode of functioning, the first transducer is in line with direction of sound and the first extruded channel, and wherein the second transducer is in-line with the direction of sound and, in line with the second extruded channel.

26. A connector permitting acoustic and digital transmission from a stethoscope, the connector comprising:
a first piece communicatively coupled to a chest piece of the stethoscope through a first extruded channel;
a second piece communicatively coupled to an earpiece of the stethoscope through a second extruded channel;
an inner element at least partially within the first piece and displaceable within the first piece, wherein the inner element includes at least two first-piece end openings on an end of the first piece and at least two second-piece end openings on an end of the second piece;
an inner element channel within the inner element in line with the first extruded channel and the second extruded channel, in a first position to provide an acoustic mode of functioning, wherein one of the first-piece end openings and second-piece end openings are collinear with the inner element channel, the first extruded channel, and the second extruded channel, and wherein the first extruded channel, the inner element channel, and the second extruded channel have diameters that decrease in a direction of sound;
a first transducer inside the inner element past one of the first-piece end openings to substantially block acoustic transmission from the first extruded channel;
a second transducer inside the inner element before one of the second-piece end openings, wherein, in a second position, the first transducer is in line with the first extruded channel and the second transducer is configured to be in line with the second extruded channel to provide an electronic mode of functioning;
a switch configured to displace the inner element between the first position and the second position so as to switch the connector between the acoustic mode and the electronic mode; and
a first centre rod and a second centre rod configured to provide support along a longitudinal axis along which the inner element displaces.

27. The connector of claim 26, wherein the first centre rod has its first end support at the first piece and its second end support at the inner element, wherein the second centre rod has its first end support at the second piece and its second end support at the inner element where the first end rod ends, and wherein the first end rod and the second end rod are collinear and co-axial.

28. The connector of claim 26, further comprising:
a first locking coupler, wherein the inner element includes a first end and a second end, wherein the first end includes at least two openings and wherein the second end includes at least a first acoustic opening on the first piece side of the inner element that includes a hemispherical cam profile to receive a first locking coupler.

29. The connector of claim 26, wherein, in the first position, a first opening is in line with the first extruded channel and extends into the inner element channel that traverses a length of the inner element, and wherein, in the second position, a second opening is in line with the first extruded channel and in line with the first transducer in-line and behind the second opening.

30. The connector of claim 26, wherein, when the switch moves from the first position to the second position, the inner element channel is in line with the first extruded channel, and wherein when the switch moves from the second position to the first position, the first transducer is in line with the first extruded channel.

31. The connector of claim 26, wherein, in the acoustic mode of functioning, the first extruded channel, the inner element channel, and the second extruded channel are collinear and co-axial, and wherein, in the electronic mode of functioning, the first transducer is in line with direction of sound and the first extruded channel, and wherein the second transducer is in-line with the direction of sound and, in line with the second extruded channel.

32. A connector permitting acoustic and digital transmission from a stethoscope, the connector comprising:
a first piece communicatively coupled to a chest piece of the stethoscope through a first extruded channel;
a second piece communicatively coupled to an earpiece of the stethoscope through a second extruded channel;
an inner element at least partially within the first piece and displaceable within the first piece, wherein the inner element includes at least two first-piece end openings on an end of the first piece and at least two second-piece end openings on an end of the second piece, and wherein the inner element includes a first inner element and a second inner element;

an inner element channel within the inner element in line with the first extruded channel and the second extruded channel, in a first position to provide an acoustic mode of functioning, wherein one of the first-piece end openings and second-piece end openings are collinear with the inner element channel, the first extruded channel, and the second extruded channel, and wherein the first extruded channel, the inner element channel, and the second extruded channel have diameters that decrease in a direction of sound;

a first transducer inside the inner element past one of the first-piece end openings to substantially block acoustic transmission from the first extruded channel;

a second transducer inside the inner element before one of the second-piece end openings, wherein, in a second position, the first transducer is in line with the first extruded channel and the second transducer is configured to be in line with the second extruded channel to provide an electronic mode of functioning;

a switch configured to displace the inner element between the first position and the second position so as to switch the connector between the acoustic mode; and a first electronic board in the first inner element and configured to receive connector pins from a second electronic board in the second inner element to charge a battery to be used in an electronic wireless mode of functioning and power the first electronic board.

33. The connector of claim 32, further comprising:

a first locking coupler, wherein the inner element includes a first end and a second end, wherein the first end includes at least two openings and wherein the second end includes at least a first acoustic opening on the first piece side of the inner element that includes a hemispherical cam profile to receive a first locking coupler.

34. The connector of claim 32, wherein, in the first position, a first opening is in line with the first extruded channel and extends into the inner element channel that traverses a length of the inner element, and wherein, in the second position, a second opening is in line with the first extruded channel and in line with the first transducer in-line and behind the second opening.

35. The connector of claim 32, wherein, when the switch moves from the first position to the second position, the inner element channel is in line with the first extruded channel, and wherein when the switch moves from the second position to the first position, the first transducer is in line with the first extruded channel.

36. The connector of claim 32, wherein, in the acoustic mode of functioning, the first extruded channel, the inner element channel, and the second extruded channel are collinear and co-axial, and wherein, in the electronic mode of functioning, the first transducer is in line with direction of sound and the first extruded channel, and wherein the second transducer is in-line with the direction of sound and, in line with the second extruded channel.

* * * * *